United States Patent [19]

Stetter et al.

[11] 4,302,315

[45] Nov. 24, 1981

[54] GAS SENSING UNIT

[75] Inventors: Joseph R. Stetter, Naperville, Ill.; Raymond B. Cromer, New York, N.Y.

[73] Assignee: Becton, Dickinson and Company, Paramus, N.J.

[21] Appl. No.: 160,771

[22] Filed: Jun. 18, 1980

[51] Int. Cl.$^3$ ............................................. G01N 27/46
[52] U.S. Cl. ................................. 204/195 R; 204/1 T
[58] Field of Search ................... 204/195 R, 1 Y, 1 B, 204/1 N; 429/40, 42; 128/635

[56] References Cited

U.S. PATENT DOCUMENTS

| | | | |
|---|---|---|---|
| 3,719,576 | 3/1973 | Macur | 204/195 P |
| 3,726,777 | 4/1973 | Macur | 204/195 R |
| 3,776,832 | 12/1973 | Oswin et al. | 204/195 R |
| 3,824,167 | 7/1974 | Oswin et al. | 204/195 R |
| 3,900,382 | 8/1975 | Brown | 204/195 M |
| 3,909,386 | 9/1975 | Oswin et al. | 204/195 R |
| 3,923,627 | 12/1975 | Niedrach et al. | 204/195 M |
| 3,926,766 | 12/1975 | Niedrach et al. | 204/195 P |
| 3,954,590 | 5/1976 | Czuha | 204/195 W |
| 3,992,267 | 11/1976 | Oswin et al. | 204/1 T |
| 4,001,103 | 1/1977 | Blurton et al. | 204/195 R |
| 4,052,268 | 10/1977 | Blurton et al. | 204/1 T |
| 4,073,698 | 2/1978 | Blurton et al. | 204/1 T |
| 4,127,462 | 11/1978 | Blurton et al. | 204/195 R |
| 4,201,634 | 5/1980 | Stetter | 204/1 T |

*Primary Examiner*—G. L. Kaplan

[57] ABSTRACT

Methods and apparatus are provided for sensing reducible gases in the environment. The invention herein utilizes electrochemical sensing procedures incorporating gold as the sensing electrode in combination with a material selected from the group of iridium and ruthenium as the counterelectrode. This combination avoids the usual polarization at the anode in prior arrangements of this kind and the gradual degradation in the degree of sensing specificity for sensing, for example, $NO_2$ and $Cl_2$. In those instances wherein a three electrode system is used, the third or reference electrode may be comprised of platinum, iridium or ruthenium.

9 Claims, No Drawings

GAS SENSING UNIT

BACKGROUND OF THE INVENTION

This invention relates generally to an electrochemical cell for use in a gas detector unit, and more particularly, to a cell for sensing reducible gases including, for example, $NO_2$, $Cl_2$, $O_3$, $ClO_2$ and $O_2$. This is achieved by the use of gold as the sensing electrode in combination with a material selected from the group of iridium and ruthenium as the counterelectrode, and preferably iridium. For three electrode sensors wherein a reference electrode is utilized, preferably the material will be selected which is similar to the counterelectrode material. However, the material may be selected from platinum, iridium and ruthenium. The effect of this combination of materials utilized in the electrodes of the sensor of the invention is a more stable continuously operating cell, not subject to the usual degradation of prior art cells. This invention is an improvement over the inventions described in U.S. Pat. Nos. 3,992,267, issued Nov. 16, 1976; 3,824,167, issued July 16, 1974; 3,776,832 issued Dec. 4, 1973 and 3,909,386, issued Sept. 30, 1975. Each of these patents is incorporated by reference in its entirety herein.

With ever increasing concern about pollution of our environment and our increasingly sophisticated knowledge with respect to the presence of polluting materials in the environment, attempts have been made to develop systems which will protect us by warning of increases in the concentration of certain substances in the ambient to a level which is dangerous to our existence. One such device which has been developed in recent years is a gas sensor for sensing the presence of such gases adjacent a work area, for example. As will be appreciated, it is important that such sensors continue to operate over a period of time so that certain enclosed areas are protected, for example, such as mines where certain levels of concentration of gases may cause death if exposure is for a specific period of time. It is important, also, from a manpower standpoint that the instruments need not be continuously attended to because of any rapid deterioration of the sensing capacity thereof.

However, electrochemical gas sensors, for example, are subject to certain limitations over a period of time merely because of the chemical nature in which they operate, in the sense that the sensing capacity degrades. For example, in the past, in electrochemical sensors for detecting reducible gases such as $NO_2$ and $Cl_2$, where both the sensing and counterelectrode are comprised of gold diffusion electrodes, and wherein sulfuric acid is used as the electrolyte, a large irreversible polarization of the gold counterelectrode occurs during detection. This polarization causes sluggish response characteristics during detection. Whereas such sluggish responses may not always be of substantial importance, there are instances where the rapid sensing of the presence of a gas is important. Another example of such degradation over a period of time involves the use of platinum as the counterelectrode material. In such an arrangement, there is gradual degradation in the sensor specificity over a period of time with a gradual increase of, for example, an interferring carbon monoxide sensitivity signal.

STATEMENT OF THE INVENTION

With this invention, by contrast, vastly improved sensor performance characteristics are achieved, including fast response time of the signal rise and decay, repeatability of the signal magnitude and zero, selectivity, and long-term stability of the system's performance, for sensing reducible gases. The above, is achieved in the use of an electrochemical sensor with a gold sensing electrode in combination with a counterelectrode comprised essentially of iridium or ruthenium, and preferably iridium. When it is desired to have a three electrode sensor system, with a reference electrode for imparting a fixed potential on the sensing electrode, the reference electrode will be comprised of a member of the group consisting of platinum, iridium and ruthenium. Preferably, and conveniently, the reference electrode will be comprised of the same material as the counterelectrode. Such a combination provides a fast reversible redox reaction and little or no interference from CO. For a more complete description of an arrangement of three electrode electrochemical cell systems whose arrangement is useful in the practice of the invention here, reference is made to the structure as generally shown in U.S. Pat. No. 3,909,386.

In constructing the electrodes of the invention, it is preferable that a porous substrate is utilized. In addition, the substrate should be hydrophobic so as to optimize the interface between the active material of the electrode and the gas. In this case, gold is the active sensing material and preferably iridium is the active material of the counterelectrode. Preferably, sintered polytetrafluoroethylene is utilized as the porous substrate material. However, other porous materials such as sintered polyethylene or polypropylene, or silicon membranes may also be utilized. Thus, in an $NO_2$ sensor, for example, gold is deposited on a porous polytetrafluoroethylene substrate and iridium is also deposited on such porous substrate. In the construction of the sensor for sensing $NO_2$, it is preferable to have an additional electrode as the reference electrode for imparting a fixed potential on the sensing or gold electrode. In this connection reference is made to FIG. 3 of U.S. Pat. No. 3,909,386 for the general construction of an electrolyte containing chamber. For sensing $NO_2$, the electrolyte may be sulfuric acid. As shown in U.S. Pat. No. 3,909,386, the sensing electrode is positioned at one end of the chamber and the counterelectrode and reference electrode are positioned at the opposite end thereof. However, other constructions may provide for all of the electrodes positioned at one end of the chamber in a single plane.

As purely illustrative of the results achieved in accordance with this invention, one may note Table I below which lists the test results and comparative data in a gas sensing unit with gold as the sensing electrode in each case and with gold, platinum or iridium used as the counterelectrode.

TABLE I

| Sensor No. | Counter-electrode Material | 90% Rise In Seconds | 90% Decay In Seconds | Ratio $CO:NO_2$ |
|---|---|---|---|---|
| 1 | Gold | 90 | 60 | 400 |
| 2 | Gold | 100 | 70 | 350 |
| 3 | Platinum | 30 | 15 | 200 |
| 4 | Platinum | 30 | 15 | 168 |
| 5 | Iridium | 30 | 10 | 1020 |
| 6 | Iridium | 30 | 10 | 2100 |

As will be apparent from a review of the results noted in Table I, the response time using a platinum counterelectrode compares well with a sensor using an iridium counterelectrode. However, the selectivity ratio of CO to $NO_2$ using a platinum electrode is poor whereas the ratio is extraordinarily higher with the use of an iridium electrode. Using a gold counterelectrode, neither the response time nor selectivity compares well with the use of the iridium electrode in accordance with this invention.

Thus, as will be appreciated, by including gold as the sensing electrode in an electrochemical cell for use in gas detection of reducible gases and by including a member selected from the group of iridium and ruthenium as the counterelectrode, an improved electrochemical sensor is provided which alleviates the sluggish response characteristics of the prior art and the specificity degradation. By the appropriate selection of materials for the electrodes in accordance with this invention, large irreversible anodic polarization is avoided which is responsible for the sluggish response characteristics and the selection also exhibits minimum sensitivity to an interferring carbon monoxide signal which is apparent in prior art constructions.

While the forms of construction herein disclosed form preferred embodiments of this invention, this invention is not limited to those specific forms of construction, and changes can be made therein without departing from the scope of this invention which is defined in the appended claims. For example, practitioners in the art may choose other forms of sensor cells such as those referred to in the prior art patents noted above as long as the combination of a gold sensing electrode and a counterelectrode selected from iridium and ruthenium is utilized. The appropriate electrolyte in proper concentration will be selected depending upon the reducible gas involved and the environment in which the sensor is to be used.

What is claimed is:

1. An electrochemical sensor for the detection of electrochemically reducible gases comprising
   (a) a chamber containing an electrolyte;
   (b) a sensing electrode in contact with said electrolyte in said chamber;
   (c) a counterelectrode in contact with said electrolyte in said chamber;
   (d) said sensing electrode is comprised of gold bonded to a porous hydrophobic membrane;
   (e) said counterelectrode is a member selected from the group consisting of iridium and ruthenium; and
   (f) said counterelectrode is bonded to a porous hydrophobic membrane.

2. The sensor of claim 1, further characterized by
   (a) said counterelectrode is iridium.

3. The sensor of claim 1, further characterized by
   (a) said porous substrate is sintered polytetrafluoroethylene.

4. The sensor of claim 1, further characterized by
   (a) a reference electrode in contact with said electrolyte in said chamber;
   (b) means forming an electrical connection between said sensing electrode and said reference electrode; and
   (c) said reference electrode imparting a fixed potential on said sensing electrode.

5. The sensor of claim 4, further characterized by
   (a) said reference electrode is selected from the group consisting of platinum, iridium and ruthenium.

6. An electrochemical sensor for detecting electrochemically reducible gases comprising
   (a) a chamber containing an electrolyte;
   (b) a sensing electrode in contact with said electrolyte in said chamber and comprised essentially of gold;
   (c) a counterelectrode in contact with said electrolyte in said chamber and comprised essentially of iridium;
   (d) electrical connection means for measuring the current flowing between said sensing electrode and said counterelectrode; and
   (e) means in said electrical connection means for indicating said measured current.

7. The sensor of claim 6, further characterized by
   (a) said sensing electrode and said counterelectrode are bonded to a porous hydrophobic substrate.

8. The sensor of claim 7, further characterized by
   (a) said porous hydrophobic substrate is a member selected from the group consisting of sintered polytetrafluoroethylene, sintered polyethylene, sintered polypropylene and a silicon membrane.

9. The sensor of claim 6, further characterized by
   (a) a reference electrode comprised essentially of iridium.

* * * * *